US00PP09904P

United States Patent [19]

Glicenstein

[11] Patent Number: Plant 9,904

[45] Date of Patent: May 27, 1997

[54] CHRYSANTHEMUM PLANT NAMED 'BLUSHING CHRISTINE'

[75] Inventor: Leon Glicenstein, Salinas, Calif.

[73] Assignee: Yoder Brothers, Inc., Barberton, Ohio

[21] Appl. No.: 605,611

[22] Filed: Feb. 22, 1996

[51] Int. Cl.[6] ..... A01H 5/00

[52] U.S. Cl. ..... Plt./76

[58] Field of Search ..... Plt./76, 80, 81, Plt./82

[56] References Cited

U.S. PATENT DOCUMENTS

P.P. 8,988 11/1994 VandenBerg ..... Plt./81
4,616,099 10/1986 Sparkes ..... 47/58

OTHER PUBLICATIONS

Broertjes et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Seale, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of Chrysanthemums", Euphytica, 15:156–162.

Dowrick, et al., 1966, "The induction of mutations in chrysanthemum using X–and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Blushing Christine particularly characterized by its flat capitulum form; decorative capitulum type; greyed-red ray floret color; diameter across face of capitulum of 60 to 64 mm when fully opened; branching pattern is spreading and prolific, with 7 to 9 laterals developing after pinch when grown outside under natural daylength in fall flowerings; natural season flower date of August 24 to September 2 when planting rooted cuttings on June 17 to 21 in Salinas, Calif., and of September 23 to October 5 when planting rooted cuttings June 15 to 18 in Hightstown, N.J.; plant height of 33 to 39 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Blushing Christine.

Blushing Christine, identified as 7974 (89-755H01), is a product of a mutation induction program. The new cultivar was discovered and selected by inventor Leon Glicenstein on Sep. 1, 1993 in a controlled environment in Salinas, Calif. as one flowering plant within a flowering block established as rooted cuttings from stock plants which had been exposed as unrooted cuttings to an X-ray source of 2000 rads in Fort Myers, Fla. on Jan. 28, 1993. The irradiated parent cultivar was the cultivar Christine, disclosed in U.S. Plant Pat. No. 8,988 and described as a flat decorative garden mum with coral-red flower color.

The irradiation program resulting in Blushing Christine has as its primary objective the expansion of color ranges of the parent cultivar Christine. The irradiation program comprised irradiation of cuttings of the parent cultivar at irradiation levels of 1500, 1750 and 2000 rads. A total of 466 cuttings harvested from a total of 225 irradiated plants were planted on Jun. 21, 1993. Of these, 4 initial selections were made, which selections were then revegetated and reflowered. One selection died during the revegetation process. Three consecutive flowerings resulted in discarding 1 of the original selections on Oct. 17, 1994. The remaining 2 selections were maintained as PIs (Possible Introductions) and further trialed in Salinas, Calif., Hightstown, N.J. and Leamington, Ontario, Canada, ultimately resulting in the decision to introduce one selection as Blushing Christine, and the other selection as Bold Christine, disclosed in pending application Ser. No. 08/605,820.

The first act of asexual reproduction of Blushing Christine was accomplished when vegetative cuttings were taken from the initial selection in November of 1993 in a controlled environment in Salinas, Calif., by technicians working under supervision of Leon Glicenstein.

Horticultural examination of controlled flowerings of successive plantings has shown that the unique combination of characteristics as herein disclosed for Blushing Christine are firmly fixed and are retained through successive generations of asexual reproduction.

Blushing Christine has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Blushing Christine, which, in combination, distinguish this Chrysanthemum as a new and distinct cultivar:

1. Flat capitulum form.
2. Decorative capitulum type.
3. Greyed-red ray floret color.
4. Diameter across face of capitulum of 60 to 64 mm when fully opened.
5. Branching pattern is spreading and prolific, with 7 to 9 laterals developing after pinch when grown outside under natural daylength in fall flowerings.

6. Natural season flower date of August 24 to September 2 when planting rooted cuttings on June 17 to 21 in Salinas, Calif., and of September 23 to October 5 when planting rooted cuttings Jun. 15 to 18 in Hightstown, N.J.

7. Plant height of 33 to 39 cm when grown in fall under natural daylength with no growth regulators.

8. Durable, uniform performance.

The accompanying photographic drawing is a color photograph of Blushing Christine grown as a pinched garden mum under natural season outside conditions in Salinas, Calif., with the colors being as nearly ture as possible with illustrations of this type. Plants were grown outside and dug and transplanted in 15 cm pots for photography purposes.

Of the commercial cultivars know to the inventor, the most similar in comparison to Blushing Christine is the parent cultivar Christine. All traits of Blushing Christine are similar to those of Christine, except for the ray floret color and the plant height. The ray floret color of Blushing Christine is greyed-red (R.H.S. 180D, with the center of the flower 182C), while the ray floret color of Christine is described as coral-red (R.H.S. 51A to 51B). Blushing Christine has a slightly shorter plant height than Christine.

In the following description color references are made to The Royal Horticultural Society Colour Chart. The color values were determined on plant material grown as a pinched garden mum grown outdoors in Salinas, Calif. on Sep. 1, 1995.

Classification:

*Botanical.*—*Dendranthema grandiflora* cv Blushing Christine.

*Commercial.*—Flat decorative garden mum.

INFLORESCENCE

A. Capitulum:

*Form.*—Flat

*Type.*—Decorative.

*Diameter across face.*—60 to 64 mm when fully opened.

B. Corolla of ray florets:

*Color (general tonality from a distance of three meters)* .—Greyed-red.

*Color (upper surface).*—180D, with center of flower 182C.

*Color (under surface).*—180D.

*Shape.*—Cross-section flat, longitudinal section straight. Ray floret tips rounded.

C. Corolla of disc florets:

*Color (mature).*—14A.

*Color (immature).*—14A, tinged with 144C.

D. Reproductive organs:

*Androecium.*—Present on disc florets only; scant pollen.

*Gynoecium.*—Present on both ray and disc florets.

PLANT

A. General appearance:

*Height.*—33 to 39 cm when grown in fall under natural daylength with no growth regulators.

*Branching pattern.*—Spreading and prolific, with 7 to 9 laterals developing after pinch when grown outside under natural daylength in fall flowerings.

B. Foliage:

*Color (upper surface).*—147A.

*Color (under surface).*—147B.

*Shape.*—Small, lobed, moderately serrated.

What is claimed is:

1. A new and distinct Chrysanthemum plant named Blushing Christine, as described and illustrated.

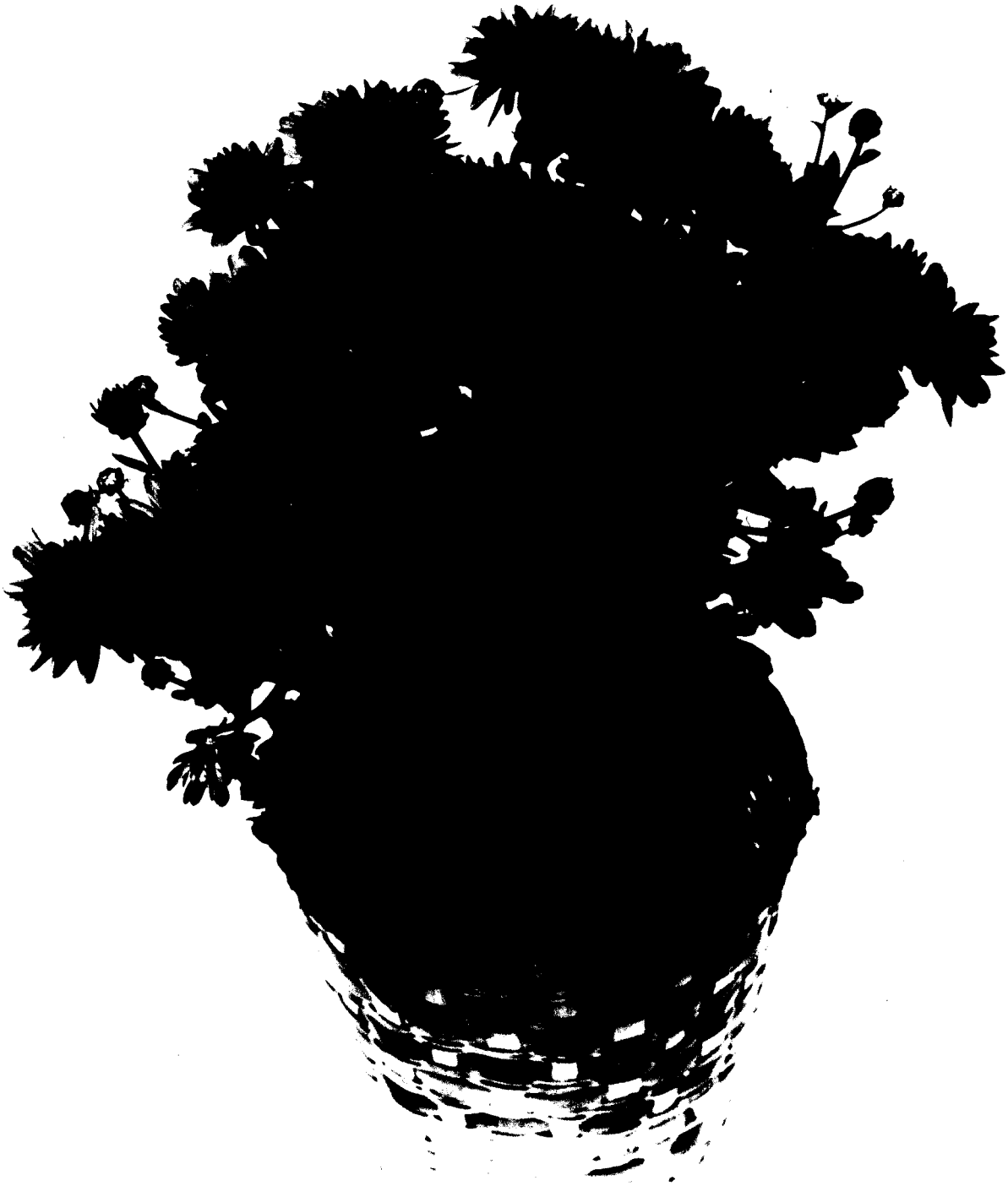

* * * * *